(12) United States Patent
Kuhl (10) Patent No.: US 9,309,125 B2
(45) Date of Patent: Apr. 12, 2016

(54) PROCESS AND SYSTEM FOR GENERATING SYNTHESIS GAS

(71) Applicant: CCP TECHNOLOGY GMBH, Munich (DE)

(72) Inventor: Olaf Kuhl, Greifswald (DE)

(73) Assignee: CCP Technology GmbH (DE)

( * ) Notice: Subject to any disclaimer, the term of this patent is extended or adjusted under 35 U.S.C. 154(b) by 0 days.

(21) Appl. No.: 14/129,134

(22) PCT Filed: Dec. 20, 2012

(86) PCT No.: PCT/EP2012/005310
§ 371 (c)(1),
(2) Date: Jul. 24, 2014

(87) PCT Pub. No.: WO2013/091879
PCT Pub. Date: Jun. 27, 2013

(65) Prior Publication Data
US 2014/0364516 A1    Dec. 11, 2014

(30) Foreign Application Priority Data

Dec. 20, 2011 (DE) .......................... 10 2011 122 562
May 4, 2012 (DE) .......................... 10 2012 008 933
May 29, 2012 (DE) .......................... 10 2012 010 542

(51) Int. Cl.
| C01B 3/24 | (2006.01) |
|---|---|
| C01B 31/18 | (2006.01) |
| C10J 3/00 | (2006.01) |
| C10K 3/06 | (2006.01) |
| C10G 2/00 | (2006.01) |
| C01B 31/02 | (2006.01) |
| B01J 19/12 | (2006.01) |
| C07C 1/04 | (2006.01) |
| B01J 19/24 | (2006.01) |

(52) U.S. Cl.
CPC ............... *C01B 31/18* (2013.01); *B01J 19/126* (2013.01); *B01J 19/245* (2013.01); *C01B 3/24* (2013.01); *C01B 31/02* (2013.01); *C07C 1/041* (2013.01); *C07C 1/0485* (2013.01); *C10G 2/32* (2013.01); *C10G 2/34* (2013.01); *C10J 3/00* (2013.01); *C10K 3/06* (2013.01); *B01J 2219/0898* (2013.01); *B01J 2219/1206* (2013.01); *B01J 2219/24* (2013.01); *C01B 2203/0255* (2013.01); *C01B 2203/0272* (2013.01); *C01B 2203/062* (2013.01); *C01B 2203/0833* (2013.01); *C01B 2203/0861* (2013.01); *C01B 2203/1235* (2013.01); *C10G 2400/04* (2013.01); *C10J 2300/094* (2013.01); *C10J 2300/0943* (2013.01); *C10J 2300/0973* (2013.01); *C10J 2300/1659* (2013.01); *C10J 2300/1884* (2013.01)

(58) Field of Classification Search
CPC .......................... C01B 3/24; C01B 2203/0805
See application file for complete search history.

(56) References Cited

U.S. PATENT DOCUMENTS

2003/0024806 A1    2/2003    Foret

FOREIGN PATENT DOCUMENTS

| CN | 101432395 | 5/2009 |
|---|---|---|
| DE | 10 2007 005 965 | 8/2008 |
| EP | 0 219 163 | 4/1987 |
| EP | 1 270 508 | 1/2003 |
| GB | 365912 | 4/1931 |
| GB | 2 265 380 | 9/1993 |
| GB | 2 265 382 | 9/1993 |
| WO | 00/06671 | 2/2000 |

*Primary Examiner* — Sudhakar Katakam
(74) *Attorney, Agent, or Firm* — Tarolli, Sundheim, Covell & Tummino LLP (57) ABSTRACT

A method and an apparatus for generating synthesis gas using hydrocarbons and water are described. In further embodiments of the method and the apparatus, synthesis gases having any desired CO/hydrogen ratio and/or synthetic functionalized and/or non-functionalized hydrocarbons are generated. With this method, a hydrocarbon containing fluid may be transformed into a synthesis gas having variable hydrogen content without generating significant amounts of CO2. Further, hydrogen and different forms of carbon may be obtained as by-products.

13 Claims, 4 Drawing Sheets

PROCESS AND SYSTEM FOR GENERATING SYNTHESIS GAS

RELATED APPLICATIONS

This application corresponds to PCT/EP2012/005310, filed Dec. 20, 2012, which claims the benefit of German Applications Nos. 10 2011 122 562.9, filed Dec. 20, 2011; 10 2012 008 933.3, filed May 4, 2012; and 10 2012 010 542.8, filed May 29, 2012, the subject matter, of which are incorporated herein by reference in their entirety.

BACKGROUND OF THE INVENTION

The present invention relates to a method and a plant for generating synthesis gas from hydrocarbons and water.

SUMMARY OF THE INVENTION

Significant parts of the world's economy are based on crude oil as raw material or as source of energy. Thus, Otto and Diesel fuel for individual and goods transport, heavy oil for ships and as fuel for electricity plants as well as light oil for the heating of family homes are produced from crude oil. Also, many raw materials for the chemical industry are derived, directly or indirectly, from crude oil. At present, significant efforts are undertaken to substitute crude oil products with other raw materials or alternative processes. In the energy sector, natural gas and renewable energies are used instead of crude oil in the operation of power plants. Electric engines, natural gas engines and hydrogen fuel cells are tested for traffic applications, but they could not be commercially established.

There are attempts to produce oil products from natural gas or coal on an industrial scale. For example, processes for the transformation of natural gas into liquid fuels are known (so called Gas-to-Liquid or GtL-processes). Nevertheless, these processes generally involve significant $CO_2$-emissions and high costs. In addition, they are usually not able to provide hydrogen independently of CO or $CO_2$. Therefore, these attempts are usually limited, due to economic and ecological reasons, to a few isolated applications.

Synthesis gas, or abbreviated syngas, is a gas mixture of carbon monoxide and hydrogen that can also contain carbon dioxide. For example, the syngas is generated by the gasification of carbon containing fuel to a gaseous product, the syngas, having a certain calorific value. The synthesis gas has approximately 50% of the energy density of natural gas. The synthesis gas may be burned and thus used as a fuel source. The synthesis gas can also be used as an intermediate product in the generation of other chemical products. For example, the synthesis gas may be generated by the gasification of coal or waste. In the generation of synthesis gas, carbon may react with water, or a hydrocarbon may react with oxygen. There are commercially available technologies for processing synthesis gas in order to generate industrial gases, fertilisers, chemicals and other chemical products. However, most known technologies (e.g. water-shift-reaction) for the generation and transformation of synthesis gas have the problem that the synthesis of the required amount of hydrogen causes the generation of a larger amount of surplus $CO_2$ which is finally emitted into the atmosphere as a climate damaging gas. Another known technology for the production of synthesis gas, the partial oxidation of methane according to the equation $2CH_4+O_2 \rightarrow 2CO+4H_2$ can reach a maximum ratio of $H_2$:CO of 2.0. However, the disadvantage is the use of pure oxygen that is energy intensively produced.

EP 0 219 163 A discloses a method for generating synthesis gas wherein hydrocarbons are decomposed in a first reactor chamber so as to form carbon and hydrogen, and wherein the carbon is transported into a second reaction chamber and is brought into contact with water for reaction.

WO 00/06671 A1 discloses a method for generating synthesis gas wherein, in presence of air, a biological material is transformed into carbon and waste gasses such as water and CO2 in a first reactor chamber, and wherein synthesis gas is formed from said carbon and steam in a second reaction chamber.

Therefore, a first problem to be solved by the invention is to transform a hydrocarbon containing fluid into synthesis gas with a variable hydrogen content, without generating significant amounts of $CO_2$.

In particular, a method for generating synthesis gas comprises decomposing a hydrocarbon containing fluid into carbon and hydrogen by means of introduction of energy that is at least partially provided by heat, wherein the carbon and the hydrogen have a temperature of at least 200° C. after the decomposing step. A portion of the carbon generated by the decomposing step is then brought into contact with water at a temperature between 800 and 1700° C., wherein the carbon generated by the decomposing step cools down not more than 50% in ° C. with respect to its temperature after the decomposing step upon bringing the carbon in contact with water. Here, at least a portion of the water, together with the carbon generated by the splitting process, is transformed into synthesis gas. This method enables the transformation of a hydrocarbon containing fluid into synthesis gas having a variable hydrogen content, without generating significant amounts of $CO_2$. In an advantageous way, at least part of the energy, required for providing the carbon (by splitting of a hydrocarbon), is introduced in form of heat for the transformation. Additionally, hydrogen and different varieties of carbon may be produced as by-products.

This is particularly true, if the decomposing step takes place at a temperature over 1000° C. and the carbon is brought into contact with the water at a temperature of at least 1000° C., particularly at a temperature between 1000° C. and 1200° C., since in this case no or only a smaller additional amount of heat needs to be provided for the transformation. Preferably, the heat required to reach the temperature of 800 to 1700° C. (particularly from 1000° C. to 1200° C.) for the transformation is essentially completely provided by the heat that is used for the splitting of the hydrocarbon containing fluid. Here, essentially completely means that at least 80%, specifically at least 90% of the required heat originates from the decomposing step.

In one embodiment, the carbon obtained in the decomposing step and the hydrogen obtained in the decomposing step are both jointly brought into contact with the water. Hydrogen does not compromise the transformation and may serve as an additional heat transfer substance. This is particularly advantageous, if the carbon and the hydrogen have a temperature of 1000° C. (a preferred transformation temperature) or above. In this case, the gas after transformation is not pure water gas but a synthesis gas with a different mixing ratio.

Alternatively, the carbon obtained from the decomposing step may be separated from the hydrogen obtained from the decomposing step prior to the step of bringing the carbon into contact with water.

In order to increase the energy efficiency of the method, at least a portion of the heat of at least a portion of the carbon and/or a portion of the hydrogen obtained from the decomposing step, may be used to heat the water prior to the step of bringing the water into contact with the carbon and/or may be used to heat the process chamber, in which the water is brought into contact with the carbon. In this sense it should be noted that the synthesis gas has a temperature of 800 to 1700° C. after transformation and that at least part of its heat may be used to preheat the water prior to the step of bringing the water into contact with the carbon. It is also possible that at least part of the heat of at least a portion of the carbon and/or the hydrogen obtained from the decomposing step, and/or a portion of the synthesis gas after transformation may be used to generate electricity which can be used as energy carrier for introducing energy for the decomposing step of the hydrocarbon containing fluid.

Preferably, the energy for decomposing the hydrocarbon is primarily introduced via a plasma. This is a particularly direct and thus efficient method to introduce energy. Preferably, the decomposing step is performed in a Kvaerner reactor that enables continuous decomposing of a stream of hydrocarbons.

In the method for generating a synthesis gas, additional hydrogen and/or carbon monoxide and/or further synthesis gas may be added to the synthesis gas in order to obtain a desired composition. In the case of bringing both carbon and hydrogen into contact with water, it may be particularly useful to add additional carbon monoxide to the synthesis gas in order to reduce the $CO/H_2$ ratio. During the step of bringing essentially pure carbon into contact with water, it may be useful to add additional carbon monoxide in order to increase the $CO/H_2$ ratio. In particular, it is possible to mix the streams of two synthesis gases separately generated according to the above mentioned method (one with, the other without previous separation of carbon and hydrogen) in order to obtain a desired mixing ratio of $CO/H_2$.

Preferably, the additional hydrogen originates from the step of decomposing of a hydrocarbon containing fluid into carbon and hydrogen by introduction of energy that is at least partially performed by heat. Therefore, the decomposing step may provide the carbon necessary for the carbon water transformation and the necessary hydrogen in one step. In one embodiment, at least a portion of the hydrogen is generated by the step of decomposing of a hydrocarbon containing fluid at a temperature below 1000° C., specifically below 600° C., by means of a microwave plasma. Where additional hydrogen (more than the amount that is obtained by the production of the carbon necessary for the carbon-water transformation) is required to obtain a specific mixing ratio of a synthesis gas, it is preferred to generate said hydrogen in an energy efficient manner at low temperatures from a hydrocarbon containing fluid. Preferably, the ratio of CO to hydrogen in the synthesis gas is adjusted to a value between 1:1 and 1:3, specifically to a value of 1:2.1.

In a method for generating synthetic functionalised and/or non-functionalised hydrocarbons, in a first step, a synthesis gas is generated, as described above, and the synthesis gas is brought into contact with a suitable catalyst in order to cause transformation of the synthesis gas into synthetic functionalised and/or non-functionalised hydrocarbons, wherein the temperature of the catalyst and/or the synthesis gas is set or regulated to a predefined temperature range. In this way, the synthesis gas may be generated by mixing CO with hydrogen, either before or when bringing it into contact with the catalyst.

In one embodiment, transformation of the synthesis gas is performed by a Fischer-Tropsch process, specifically a SMDS process. Alternatively, transformation of the synthesis gas may be performed by a Bergius-Pier process, a Pier process or a combination of a Pier process with a MtL process. It is the choice of the process, which largely determines the nature of the synthetic functionalised and/or non-functionalised hydrocarbons.

Preferably, the hydrocarbon containing fluid to be decomposed is natural gas, methane, wet gas, heavy oil, or a mixture thereof.

The apparatus for generating synthesis gas comprises a hydrocarbon converter for decomposing a hydrocarbon containing fluid into carbon and hydrogen, wherein the hydrocarbon converter comprises at least one process chamber having at least one inlet for a hydrocarbon containing fluid and at least one outlet for carbon and/or hydrogen and at least one unit for introducing energy into the process chamber, the energy consisting at least partially of heat. Further the apparatus comprises a C converter for transformation of water and carbon, the C converter comprising at least one additional process chamber having at least one inlet for water, at least one inlet for at least carbon and at least one outlet, wherein the inlet for at least carbon is directly connected to the at least one outlet of the hydrocarbon converter. Here, the term "directly connected" describes that carbon coming out of the hydrocarbon converter does not cool down by more than 50% of its temperature in ° C., preferably not more than 20%, on its way to the C converter without the utilisation of additional energy to heat up the carbon. A separating unit, which separates the carbon from the hydrogen, may be provided between the location of the decomposing step and the at least one exit of the hydrocarbon converter. This unit may form part of hydrocarbon converter or may be located outside the hydrocarbon converter as a separate unit. A separating unit between the exit of the hydrocarbon converter and the entrance of a C converter does not compromise a direct connection as long as the above condition is met.

Preferably, the at least one unit for introducing energy into the process chamber is constructed in such a way that it is able to at least locally generate temperatures above 1000° C., specifically above 1500° C. In one embodiment, that at least one unit for introducing energy into the process chamber is a plasma unit. Particularly, if the decomposing temperature is to be kept below 1000° C., that at least one unit for introducing energy into the process chamber preferably comprises a microwave plasma unit.

For a particularly simple embodiment of the apparatus, the process chamber of the C converter is formed by an outlet pipe of the hydrocarbon converter which is connected to a supply pipe for water.

In one embodiment of the invention, a separation unit for separating the carbon and the hydrogen generated by decomposing is provided in the vicinity of the hydrocarbon converter, and separate outlets from the separation unit are provided for the separated materials, wherein the outlet for carbon is connected to the C converter.

Preferably, the hydrocarbon converter is a Kvaerner reactor that can provide the necessary temperatures for a continuous splitting of a hydrocarbon containing fluid for long operating periods.

For a simple and efficient generation of a synthesis gas having a variable mixing ratio, the apparatus may comprise at least one separate supply pipe for supplying hydrogen and/or carbon and/or a separate synthesis gas into the C converter or a downstream mixing chamber.

In one embodiment, the apparatus for generating synthesis gas comprises at least one additional hydrocarbon converter for decomposing a hydrocarbon containing fluid into carbon and hydrogen. The at least one additional hydrocarbon converter again comprises at least one process chamber having at least one inlet for the hydrocarbon containing fluid, at least one unit for introducing energy into the process chamber, wherein the energy at least partly consists of heat, and a separation unit for separating the carbon from the hydrogen, which were obtained by decomposing, the separation unit having separate outlets for carbon and hydrogen, wherein the outlet for hydrogen is connected to the separate supply pipe for hydrogen. For reasons of energy efficiency, the at least one additional hydrocarbon converter is preferably of the type that carries out decomposing at temperatures below 1000° C., specifically below 600° C., by means of a microwave plasma.

The apparatus for the transformation of a synthesis gas into synthetic functionalised and/or non-functionalised hydrocarbons comprises an apparatus for generating synthesis gas of the above specified type and a CO converter. The CO converter comprises a process chamber equipped with a catalyst, means for bringing the synthesis gas into contact with the catalyst, and a control unit for controlling or regulating the temperature of the catalyst and/or the synthesis gas to a predetermined temperature. In this way, parts of the apparatus for generating a synthesis gas can be integrated into the CO converter, e.g. a mixing chamber for CO and additional hydrogen, carbon and/or another synthesis gas. In one embodiment, the CO converter comprises a Fischer-Tropsch converter, particularly a SMDS converter. Alternatively, the CO converter may comprise a Bergius-Pier converter, a Pier converter or a combination of a Pier converter and a MtL converter. It is also possible that several CO converters of the same or of different types are present in the apparatus.

Preferably, the apparatus comprises a control unit for controlling or regulating the pressure of the synthesis gas inside the CO converter.

BRIEF DESCRIPTION OF THE DRAWINGS

Below the invention is explained in more detail with reference to certain embodiments and drawings, wherein.

DESCRIPTION OF EMBODIMENTS

It shall be noted the terms top, bottom, right and left as well as similar terms in the following description relate to the orientations and arrangements, respectively, shown in the figures and are only meant for the description of the embodiments. These terms may show preferred arrangements, but are not limiting. Further, in the different figures, the same reference numerals are used for describing the same or similar parts.

In the following specification, processes and apparatuses are described that handle "hot" materials or carry out "hot" processes. In to the context of this description, the expression "hot" shall describe a temperature above 200° C. and preferably above 300° C.

Synthesis gas is any gas that consists mainly of carbon monoxide and hydrogen. A (synthesis) gas that consists of almost equal parts of carbon monoxide and hydrogen (1:1), is called water gas. The expression synthesis gas, as used herein, encompasses water gas as a special mixture of synthesis gas.

Figure 1:
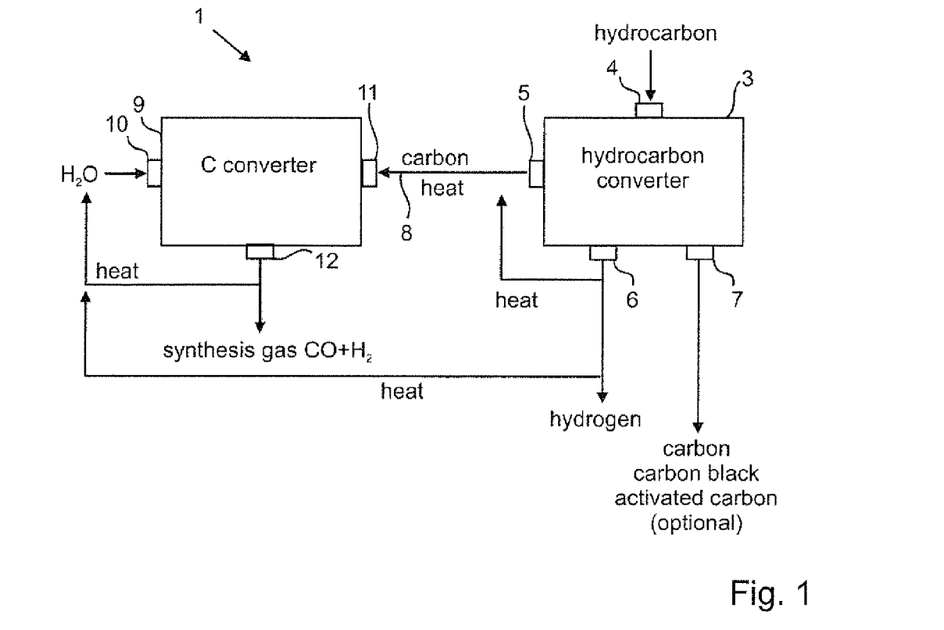
FIG. 1 is a schematic representation of a plant for generating synthesis gas.

FIG. 1 shows schematically a plant 1 for generating synthesis gas. FIG. 1 also clarifies the basic process steps for the generation of synthesis gas according to this description.

Plant 1 for generating synthesis gas comprises a hydrocarbon converter 3 that comprises a hydrocarbon inlet 4 and a first carbon outlet 5, an optional hydrogen outlet 6 as well as an optional second carbon outlet 7. Plant 1 for the generation of synthesis gas further comprises a C converter 9 having a water inlet 10, a carbon outlet 11 (also referred to as C-inlet) and a synthesis gas outlet 12 (synthesis gas exit). The hydrocarbon converter 3 and the C converter 9 are arranged such that the carbon outlet 5 of the hydrocarbon converter 3 is connected to the carbon inlet 11 of the C converter 9 via a direct connection 8, wherein the outlet 5 may directly define the carbon inlet 11 of the C converter 9. In this way, carbon can be directly transported from the hydrocarbon converter 3 into the C converter 9.

The hydrocarbon converter 3 is any hydrocarbon converter that can transform or decompose introduced hydrocarbons into carbon and hydrogen. The hydrocarbon converter 3 comprises a process chamber having an inlet for a hydrocarbon containing fluid, at least one unit for introducing decomposing energy into the fluid and at least one outlet. The decomposing energy is provided at least partially by heat, which is for instance provided by a plasma. Nevertheless, the decomposing energy may also be provided by other means and, if decomposing is primarily effected by heat, the fluid should be heated to above 1000° C. and particularly to a temperature above 1500° C.

In the described embodiment, a Kvaerner reactor is used, which provides the required heat by means of a plasma arc. However, other reactors are known which operate at lower temperatures, particularly below 1000° C., and introduce additional energy besides heat into the hydrocarbon, e.g. by means of a microwave plasma. As is further explained below, the invention considers both types of reactors (and also those which operate without plasma), in particular also both types of reactors in combination with each other. Hydrocarbon converters that operate at a temperature above 1000° C. are referred to as high temperature reactors, whereas those converters that operate at temperatures below 1000° C., particularly at temperatures between 200° C. and 1000° C., are referred to as low temperature reactors.

Within the hydrocarbon converter, hydrocarbons ($C_nH_m$) are decomposed into hydrogen and carbon by means of heat and/or a plasma. These hydrocarbons are preferably introduced into the reactor as gases. Hydrocarbons that are liquids under standard conditions may be vaporised prior to introduction into the reactor or they may be introduced as microdroplets. Both forms are denoted as fluids in the following.

Decomposing of the hydrocarbons should be done, if possible, in the absence of oxygen in order to suppress the formation of carbon oxides or water. Nevertheless, small amounts of oxygen, which might be introduced together with the hydrocarbons, are not detrimental for the process.

The Kvaerner reactor, described above, decomposes hydrocarbon containing fluids in a plasma burner at high temperatures into pure carbon (for instance as activated coal, carbon black, graphite or industrial soot) and hydrogen and, possibly, impurities. The hydrocarbon containing fluids used as starting material for the hydrocarbon converter 3 are for instance methane, natural gas, biogases, wet gases or heavy oil. However, synthetic functionalised and/or non-functionalised hydrocarbons may also be used as starting material for the hydrocarbon converter 3. After the initial decomposing step, the elements are usually present as a mixture, particularly in form of an aerosol. This mixture may, as described below, be introduced into another process in this form or the mixture may be separated into its individual elements in a separation unit, which is not shown. In the context of this patent application, such a separation unit is considered as part of the hydrocarbon converter 3, although the separation unit may be constructed as a separate unit. If no separation unit is provided, the carbon outlet 5 is the only outlet of the hydrocarbon converter 3 and directs a mixture (an aerosol) of carbon and hydrogen directly into the C converter 9. If the separation unit is provided, carbon, which is at least partially separated from hydrogen, can be directed into the C converter 9 using the carbon outlet 5. Separated hydrogen and, possibly, additional carbon may be discharged by means of the optional outlets 6 and 7.

The C converter 9 can be any suitable C converter that can generate synthesis gas (syngas) from carbon (C) and water ($H_2O$). In the embodiment of FIG. 1, within the C converter 9, $H_2O$ is passed over carbon or water steam is introduced into a stream of carbon and hydrogen and is mixed with the stream so as to be transformed according to the chemical equation $C+H_2O \rightarrow CO+H_2$. In the C converter 9, the following reactions take place:

$$C+H_2O \rightarrow CO+H_2 \; +131.38 \text{ kJ/mol endothermic}$$

$$CO+H_2O \rightarrow CO_2+H_2 \; -41.19 \text{ kJ/mol exothermic}$$

In the Boudouard equilibrium, the following reaction occurs:

$$2CO_2 \rightarrow 2CO \; +172.58 \text{ kJ/mol endothermic}$$

Since all three reaction are in equilibrium with each other, the process in the C converter 9 occurs preferably at high temperatures from 800 to 1700° C., preferred from 1000 to 1200° C., since the second reaction would be dominant at lower temperatures, wherein the heat required to reach the temperature above is primarily provided by the material issued from the hydrocarbon converter 3, as is described in more detail below. Under these conditions, the water ($H_2O$) in the C converter 9 is steam, and the water may already be introduced as steam. The supply of water during operation is controlled such that a surplus of water is avoided, so as to avoid strong cooling. In case of excessive cooling in the C converter 9, reaction 2 above would also be dominant.

The $CO_2$ converter 9 operates best at high temperatures from 1000 to 200° C. in order to repress the exothermic water shift reaction $CO+H_2O \rightarrow CO_2+H_2$ and thus to optimise the share of carbon monoxide in the synthesis gas. The reactions in the C converter 9 are known to the person skilled in the art and are thus not discussed in further detail here.

The operation of plant 1 for the generation of synthesis gas is described in more detail below, with reference to FIG. 1. In the following, it is assumed that the hydrocarbon converter 3 is a high temperature reactor of the Kvaerner type. Hydrocarbon containing fluids (specifically in gaseous form) are introduced into the hydrocarbon converter 3 via the hydrocarbon inlet 4. If the hydrocarbon is for instance methane ($CH_4$), then 1 mol carbon and 2 mol hydrogen are generated from 1 mol methane. The hydrocarbons are transformed at ca. 1600° C. in the plasma torch of the hydrocarbon converter 3 according to the following reaction equation, wherein the introduced energy is heat that is generated in the plasma by means of electric energy:

$$C_nH_m + \text{Energy} \rightarrow nC + m/2H_2$$

With appropriate process control, the Kvaerner reactor is capable of transforming almost 100% of the hydrocarbons into their components in a continuous operation.

In the following, it is assumed that the carbon and the hydrogen are separated in the hydrocarbon converter 3 and they are discharged largely separated. However, it is also possible that separation does not occur but carbon and hydrogen are discharged and introduced into the C converter 9 as a mixture. The hydrogen does not compromise the transformation process in the C converter 9, but may serve as an additional heat transfer substance. The carbon is at least partially directed directly from the carbon outlet 5 into the carbon inlet 11 of the C converter 9. The term "direct" directing from outlet 5 of the hydrocarbon converter 3 to the carbon inlet 11 of the C converter 9 shall include all such variants that do not experience cooling down of more than 50% of the temperature (preferably not more than 20%) of the directed materials. Since the carbon that exits the hydrocarbon converter 3 has a high temperature, preferably over 1000° C., the heat energy contained therein can be used to maintain the temperature necessary for the transformation process in the C converter 9, which operates at a temperature of e.g. about 1000° C.

The connection 8 between the hydrocarbon converter 3 and the C converter 9 is designed such that the carbon does not cool down much (less than 50%, preferably less than 20% with reference to the temperature) on its way from the hydrocarbon converter 3 to the C converter 9. For instance, the connection 8 may be specially insulated and/or actively heated, wherein the system is preferably not provided with additional heat—i.e. not in addition to the heat introduction in the hydrocarbon converter 3. The hydrogen that is generated in the hydrocarbon converter 3, also contains heat energy, because of the operating temperature in the hydrocarbon converter 3. Therefore, one possibility to heat connection 8 is to use the heat energy of the hydrogen that exits through hydrogen outlet 6, for heating the connection 8 between the hydrocarbon converter 3 and the C converter 9 either directly or indirectly via a heat exchanger unit.

In the C converter, water, particularly in the form of steam that is introduced through the water inlet 10 of the C converter 9, is directed over hot carbon and/or is mixed with the hot carbon. The C converter operates best at high temperatures, since it is an endothermic reaction and the competing water-shift-reaction is an exothermic reaction. The reaction, which is known to the person skilled in the art, depends on pressure and temperature and will not be described in detail. Either the amount of the water introduced into the C converter 9 or the amount of carbon can be controlled (open-loop) and/or regulated (closed-loop) by appropriate means.

$$C+H_2O \rightarrow CO+H_2; \; \Delta H=+131.38 \text{ kJ/mol}$$

Also here, the Boudouard equilibrium is the limiting factor. That is why at temperatures above 1000° C. and in the absence of a surplus of water, the mixture consists of almost exclusively carbon monoxide and hydrogen. It is advantageous to preheat the water introduced into the water inlet 10 of the C converter 9, as the C converter 9 operates preferably at temperatures >1000° C. For instance, preheating of the water may be achieved by using the heat energy contained in the hot hydrogen either directly or indirectly via a heat exchange unit to preheat the water. Preferably, the heat contained in the carbon is sufficient to heat the water to the desired temperature. Only in the case where the heat generated in the hydrocarbon converter 3 is not sufficient to reach the desired transformation temperature of about 1000° C., an optional additional heating unit for heating the C converter 9 or elements contained therein may be provided. Such a unit may also be provided as a preheating unit in the vicinity of a supply line for the water or the carbon. Such a unit may also be provided only for the start-up phase of the plant in order to bring the C converter 9 or media containing parts of the plants to a starting temperature so that the system can faster reach a desired temperature state. Heating all media containing parts exclusively via the heat generated in the hydrocarbon converter 3 might take too long in the beginning.

Hot synthesis gas ($CO+H_2$) exits the C converter 9 at a temperature of >1000° C. (depending on the operating temperature of the C converter 9). The synthesis gas that exits the C converter 9 also contains heat energy, which may be e.g. used to preheat the water introduced into the water inlet 10, either directly or indirectly via a heat exchange unit (not shown in FIG. 1). With appropriate operating parameters, i.e. a temperature between 1000 and 1200° C. (and separation of hydrogen and carbon in the hydrocarbon converter 3), a synthesis gas is generated, wherein CO and $H_2$ have a ratio of 1:1, which is called water gas. Without separation of hydrogen and carbon in the hydrocarbon converter 3 and without respective appropriate operating parameters in the C converter 9, i.e. a temperature between 1000° C. and 1200° C., a synthesis gas having a $CO/H_2$ ratio of approximately 1:3 will be produced.

As mentioned above, the hydrocarbon converter 3 may comprise a second carbon outlet 7 to discharge carbon. The carbon generated in the hydrocarbon converter 3 may be discharged—after a respective separation (or as a C—$H_2$ mixture)—in different proportions through the first carbon outlet 5 and the second carbon outlet 7. The second carbon outlet 7 is used to discharge a portion of the generated carbon that is not used in the C converter 9 to generate synthesis gas. The amount of unused carbon depends on the desired composition of the synthesis gas that shall be discharged from the C converter 9. The carbon discharged through the second carbon outlet 7 may be discharged as activated carbon, graphite, carbon black or another modification such as carbon cones or carbon discs. Depending on the form and the quality of the discharged carbon, the discharged carbon may be used as raw material for the chemical industry or the electronics industry. Possible applications are for instance the manufacture of semiconductors, the production of tires, inks, toner or similar products. The carbon generated by the hydrocarbon converter 3 is a highly pure raw material that can be processed very well.

By means of the method described above for generating synthesis gas, it is possible to transform the hot carbon from the hydrocarbon converter 3 in the C converter 9 with warm or hot water to synthesis gas without or at least without significant external energy supply. Preferably, at least 80%, specifically at least 90%, of the heat necessary to reach the transformation temperature should originate from the hydrocarbon converter 3.

Figure 2:
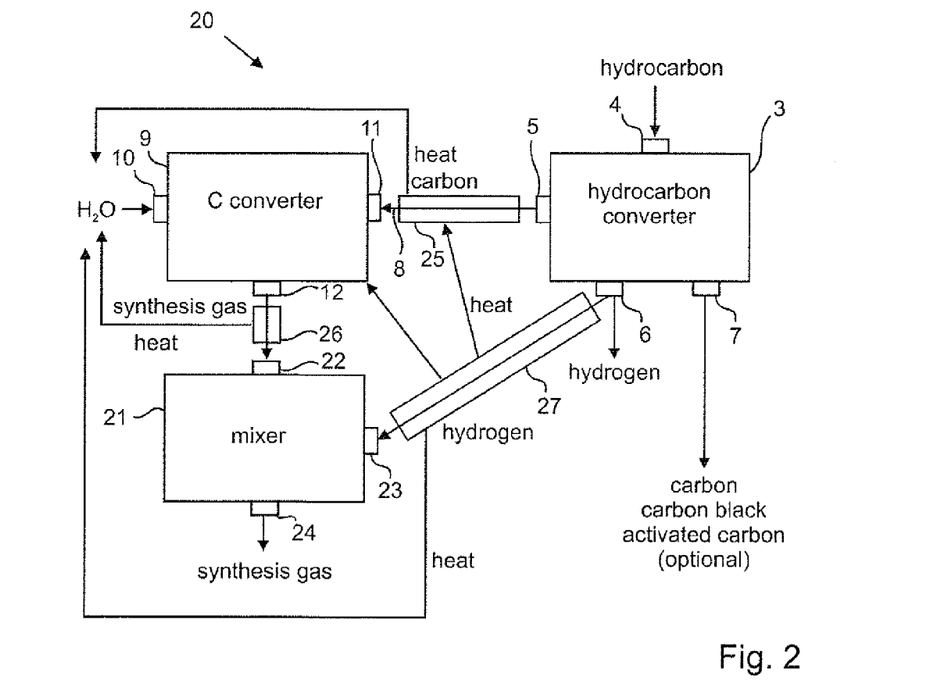
FIG. 2 is a schematic representation of an alternative plant for generating synthesis gas.

FIG. 2 shows a plant 20 for the generation of synthesis gas that comprises the above described elements of plant 4 for generating synthesis gas and a mixing chamber 21, the mixing chamber 21 comprising a synthesis gas inlet 22 for introducing synthesis gas and a $H_2$ inlet 23 for introducing hydrogen as well as a synthesis gas outlet 24 for discharging synthesis gas. The synthesis gas inlet 22 is connected to the synthesis gas outlet 12 of the C converter 9. The $H_2$ inlet 23 of the mixing chamber 21 is connected to the $H_2$ outlet 6 of the hydrocarbon converter 3. As is obvious to the skilled person, the embodiment, which introduces a C—$H_2$ mixture into the C converter 9 through the carbon outlet 5, automatically generates a synthesis gas having a mixing ratio of CO—$H_2$ of about 1:3. In such a case, the mixing chamber 21 may not be present, or the mixing chamber 21 may be used to produce a different mixing ratio, or CO may be introduced into the mixing chamber in order to reduce the $H_2$ content of the synthesis gas.

The mixing chamber 21 may be any suitable apparatus for mixing gases, and in a simple case the mixing chamber 21 may be in the form of a pipe with suitable inlets and an outlet. By means of the mixing chamber 21 and specifically by means of controlling/regulating (open/closed loop) the amount of (additional) hydrogen introduced through the $H_2$ inlet 23 of the mixing unit 21 and/or through an inlet (not shown) connected to a CO source (not shown) and/or connected to a second synthesis gas source, the mixture of the synthesis gas at the synthesis gas outlet 24 may be influenced such that a composition can be reached, which is suitable for subsequent processes. In particular, the second synthesis gas source may be a second C converter 9 operated in parallel to a first C converter. Both C converters 9 could be fed with carbon and/or hydrogen from a commonly shared hydrocarbon converter 3 or from separate converter units. In particular, a first converter may be supplied with substantially pure carbon (after separating the hydrogen), and the second converter may be supplied with a mixture of carbon and hydrogen. Here, the first C converter would produce substantially water gas having a mixing ratio of $CO:H_2$ of about 1:1 and the second C converter would produce a synthesis gas having a mixing ratio of $CO:H_2$ of about 1:3. Combing these two synthesis gases would yield a mixing ratio of $CO:H_2$ of about 1:2, wherein surplus hydrogen (from the separation step prior to introducing into the first C converter) would still be available for further increasing the mixing ratio.

For many processes, for instance the Fischer-Tropsch synthesis, the ratio of hydrogen to CO should be high. By means of the mixing chamber 21, any desired ratio of hydrogen to CO can be achieved at the synthesis gas outlet 24, for instance a ratio of 1:1, which corresponds to water gas. It is considered that only a portion of the synthesis gas and/or a portion of the hydrogen is supplied to the mixing chamber 21, whereas those portions of synthesis gas and hydrogen that are not introduced into the mixing chamber are each discharged from the process as pure gases. Therefore, it is for instance possible, a) to discharge only synthesis gas, b) to discharge only hydrogen, c) to discharge a synthesis gas mixture of CO and hydrogen or d) to discharge a stream of water gas, a stream of hydrogen and a stream of a synthesis gas mixture (any ratio between CO and hydrogen) or several synthesis gases with different ratios between carbon monoxide and hydrogen, respectively.

Furthermore, plant 20 for generating synthesis gas in FIG. 2 comprises a C heat exchange unit 25, a synthesis gas heat exchange unit 26 and a $H_2$ heat exchange unit 27. The C heat exchanger unit 25 is in thermally conductive contact with the connection 8 between the hydrocarbon converter 3 and the C converter 9 and is adapted to, if necessary, extract surplus heat not required to reach the transformation temperature in the C converter 9 from the connection or to introduce heat from other areas of the plant, if necessary.

The synthesis gas heat exchanger unit 26 is in thermally conductive contact with the connection between the C converter 9 and the mixing chamber 21 and is adapted to extract surplus heat from the connection and thus to extract surplus heat contained in the hot synthesis gas. The extracted heat may be used e.g. to preheat the water that is introduced into the C converter 9. For this heat transfer a so-called counter flow heat exchanger unit as known in the art would be particularly suitable.

The $H_2$ heat exchanger unit 27 is in thermally conductive contact with the connection between the hydrocarbon converter 3 and the mixing chamber 21 and is adapted to extract surplus heat from the connection and thus from the hot hydrogen contained therein. The heat extracted at one of the heat exchanger units 25, 26 or 27 may be used to heat other areas of the plant, and specifically to keep the C converter warm or to preheat the water that is introduced into the C converter. A portion of the heat may be converted into electricity, for instance by a steam generator and a steam turbine or by another suitable apparatus.

The operation of plant 20 for generating synthesis gas is, with respect to the operation of the hydrocarbon converter 3 and the C converter 9, similar to the above described operation of plant 1 according to FIG. 1. In plant 20 for generating synthesis gas, a desired mixing ratio of hydrogen to CO is set in the mixing chamber and is diverted through the synthesis gas outlet 24 of the mixing chamber 21, depending on the desired composition of the synthesis gas. Preferably, but not necessarily, the hydrogen is, as described, provided by the hydrocarbon converter 3. Other hydrogen sources may be considered, particularly a second hydrocarbon converter 3, particularly a low temperature hydrocarbon converter. If not the entire available amount of synthesis gas and/or the entire available amount of $H_2$ are used, those parts of the gases, e.g. synthesis gas and/or $H_2$, which are not mixed in the mixing chamber may be processed separately.

Figure 3:
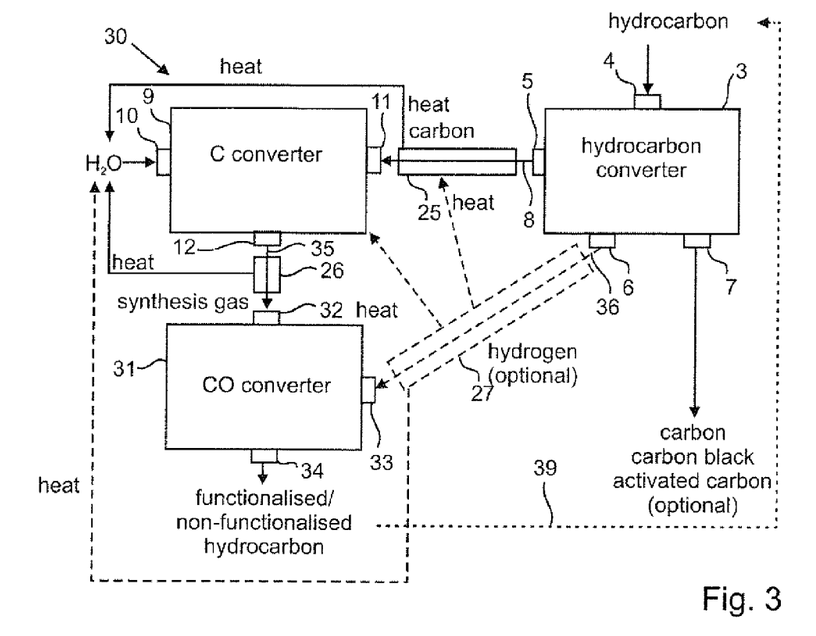
FIG. 3 is a schematic representation of a plant for generating functionalised and/or non-functionalised hydrocarbon.

FIG. 3 shows a plant 30 for the generation of synthetic functionalised and/or non-functionalised hydrocarbons that comprises a plant 10 for the generation of water gas (as shown in FIG. 1) and a CO converter 31. Those parts of the plant corresponding to plant 1 are not explained in detail in order to avoid repetitions. The CO converter 31 is located downstream from the C converter 9 and comprises a synthesis gas inlet 32 for introducing synthesis gas, a $H_2$ inlet 33 for introducing hydrogen and a hydrocarbon outlet 34 for discharging synthetic functionalised and/or non-functionalised hydrocarbons. The synthesis gas inlet 32 of the CO converter 31 is connected to the synthesis gas outlet 12 of the C converter 9 by the synthesis gas connection 35. The $H_2$ inlet 33 of the CO converter 31 is connected to the $H_2$ outlet 6 of the hydrocarbon converter 3 by the $H_2$ connection 36.

It shall be noted that the $H_2$ inlet 33 of the CO converter 31 and the $H_2$ connection 36 are optional elements. Depending on the composition of the synthesis gas, which exits from the C converter 9 and depending on the synthetic functionalised and/or non-functionalised hydrocarbons to be generated in the CO converter 31, the synthesis gas has already the right composition for further processing by CO converter 31 at the time when the synthesis gas exits from the synthesis gas outlet 12 of the C converter 9. In this case, it is not necessary to introduce hydrogen via the $H_2$ connection 36. Optionally, the $H_2$ connection 36 may also serve for introducing another material, e.g. CO for reducing the $H_2$ content of the synthesis gas or an alkene for the synthesis of an aldehyde (hydroformylation).

The plant 30 for generating hydrocarbons optionally also comprises the heat exchanger units 25, 26, 27 described in conjunction with plant 20 (FIG. 2), that is the C heat exchanger 25, the synthesis gas heat exchanger 26 and the $H_2$ heat exchanger 27, all operating in the above described way (see description to FIG. 2).

The CO converter 31 may be any CO converter for generating synthetic functionalised and/or non-functionalised hydrocarbons. In the embodiment shown in FIG. 3, the CO converter is preferably a Fischer-Tropsch converter, a Bergius-Pier converter or a Pier converter with a suitable catalyst and a control unit for temperature and/or pressure.

In one embodiment, the CO converter 31 comprises a Fischer-Tropsch converter. A Fischer-Tropsch converter catalytically transforms a synthesis gas into hydrocarbons and water. Several embodiments of Fischer-Tropsch reactors and Fischer-Tropsch processes are known to the person skilled in the art and are not explained in detail. The main reaction equations are as follows:

$nCO+(2n+1)H_2 \rightarrow H_2C_nH_{2n+2}+nH_2O$ for alkanes $nCO+2nH_2 \rightarrow C_nH_{2n}+nH_2O$ for alkenes $nCO+2nH_2 \rightarrow C_nH_{2n}+1OH+(n-1)H_2O$ for alcohols The Fischer-Tropsch processes may be carried out as high temperature processes or as low temperature processes, wherein the process temperatures are usually in the range of 200 to 400° C. Known variants of the Fischer-Tropsch process are, among others, the Hochlast synthesis, the Synthol synthesis and the SMDS process of Shell (SMDS=Shell Middle Distillate Synthesis). A Fischer-Tropsch converter typically produces a hydrocarbon compound of wet gases (propane, butane), petrol, kerosine, soft paraffin, hard paraffin, methane, Diesel fuel or a mixture of several of these. It is known to the person skilled in the art that the Fischer-Tropsch synthesis is exothermic. The heat of reaction from the Fischer-Tropsch process may be used e.g. by means of a heat exchanger unit (not shown in the figures) to preheat the water. For instance a two-step preheating process for the water to be introduced into the C converter 9, is considered, wherein a first preheating step is realised with the surplus heat of the CO converter 31 (in the embodiment of a Fischer-Tropsch converter) and subsequently a step of further heating the water by means of the heat from one or more of the heat exchanger units 25, 26, 27.

In an alternative embodiment, the CO converter 31 comprises a Bergius-Pier converter or a combination of a Pier converter with a MtL converter (MtL=Methanol-to-Liquid).

In a Bergius-Pier converter, the Bergius-Pier process, which is well known to a person skilled in the art, is carried out, wherein hydrocarbons are generated by hydrogenation of carbon with hydrogen in an exothermic chemical reaction. The range of products from the Bergius-Pier process depends on the reaction conditions and control of the reaction process. Mainly liquid products are obtained, which may be used as fuels, for instance heavy and medium oils. Known variants of the Bergius-Pier process are for instance the Konsol process and the H-Coal process.

In the above mentioned combination of a Pier converter with a MtL converter, at first synthesis gas is transformed into methanol according to the Pier process. The MtL converter is a converter that transforms methanol into petrol. A widespread process is the MtL process of ExxonMobil respectively Esso. Starting material of the MtL converter is typically methanol, for instance from the Pier converter. The exit product generated by the MtL converter typically is petrol, which is suitable for the operation of an Otto engine.

In summary, it can be said that the CO converter 31, regardless of the operating principles explained above, generates synthetic functionalised and/or non-functionalised hydrocarbons from CO and $H_2$ as its output or end products. By means of a heat exchanger unit, the process heat produced during the exothermic transformation in the CO converter 31, may be used to heat different sections of the plant or to generate electricity in order to increase the efficiency of the described plant.

As far as a mixture of hydrocarbons, which cannot be further processed directly or sold profitably as a final product after separation and specification, is obtained as exit products of the CO converter 31, these hydrocarbons, for instance methane or short-chain alkanes, may be recycled into the process described above. For this purpose, the plant 30 comprises a recycle connection 39, which can direct a portion of the synthetically generated hydrocarbons back to the hydrocarbon inlet 4 of the hydrocarbon converter 3. Depending on the composition of the recycled, synthetically generated hydrocarbons, a treatment or separation step of unsuitable hydrocarbons is carried out prior to introducing the unsuitable hydrocarbons into the hydrocarbon inlet 4.

Figure 4:
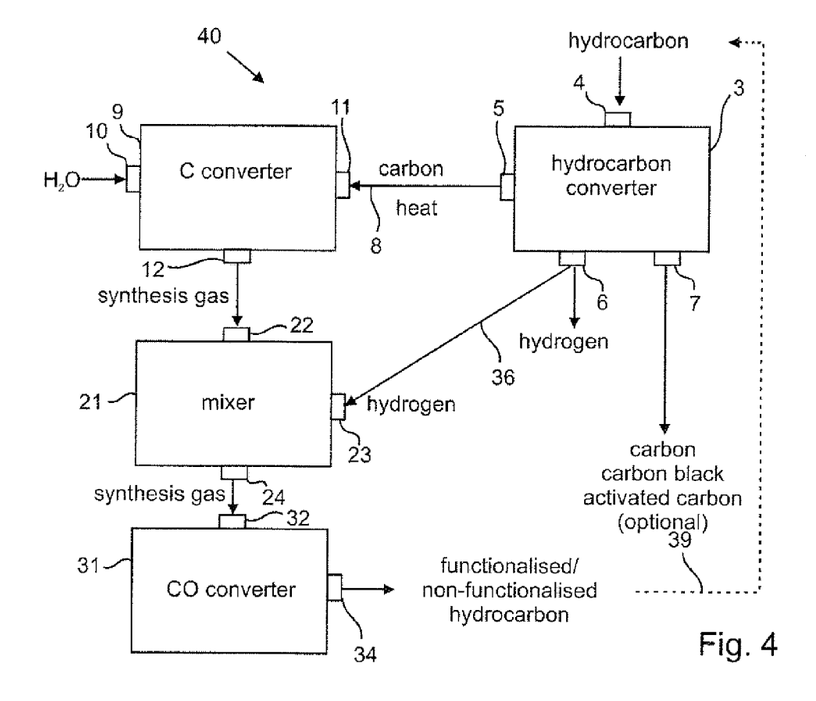
FIG. 4 is a schematic representation of another plant for generating functionalised and/or non-functionalised hydrocarbons according to another embodiment.

FIG. 4 shows a further embodiment of a plant 40 for generating synthetic functionalised and/or non-functionalised hydrocarbons. The plant 40 comprises the above described plant 20 for generating a synthesis gas as well as a CO converter 31 as described above with reference to the embodiment in FIG. 3. The synthesis gas outlet 24 of the mixing chamber 21 is connected to the synthesis gas inlet 32 of the CO converter 31. The mixing chamber 21 is set in such a way that it provides a synthesis gas adapted to the needs of the CO converter 31 in use at the synthesis gas outlet 24. The other elements of plant 40 are the same as described above and the operation of the individual elements essentially takes place in the way described above.

It is considered that, depending on the size of the plant, a plurality of hydrocarbon converters are operated in parallel in order to provide the desired transformation capacity. As mentioned above, the hydrocarbon converters may be constructed as high temperature hydrocarbon converters and/or as low temperature hydrocarbon converters. A high temperature hydrocarbon converter operates at temperatures above 1000° C. and a low temperature hydrocarbon converter operates at temperatures between 200 and 1000° C., wherein an additional source of energy, for instance a microwave unit, may be provided for directly inputting energy into the hydrocarbon in order to achieve decomposition of the hydrocarbon to carbon and hydrogen.

Figure 5:
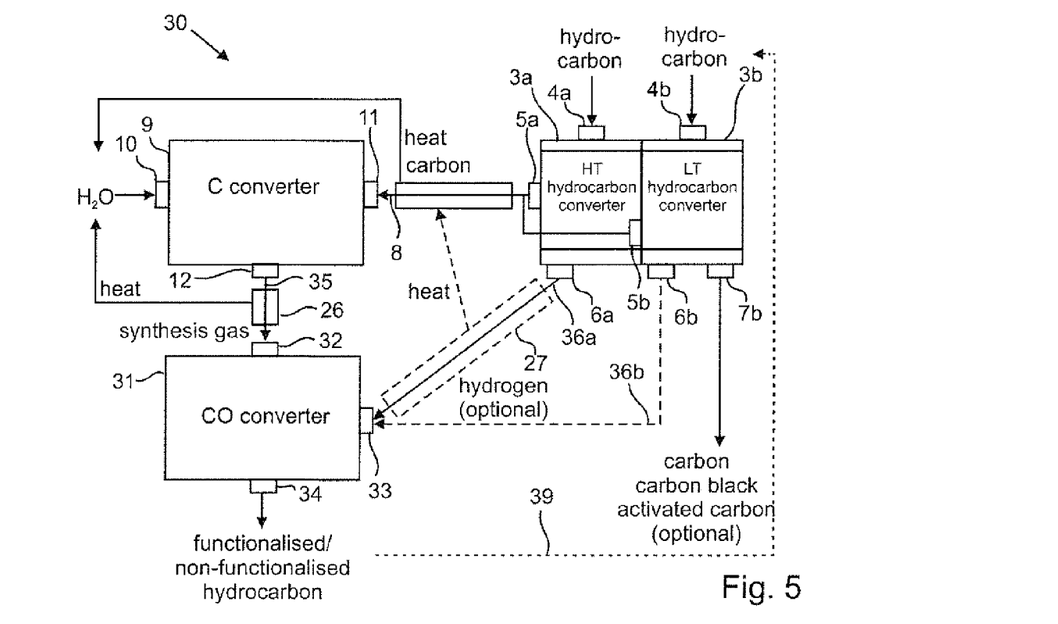
FIG. 5 is a schematic representation of a plant for generating functionalised and/or non-functionalised hydrocarbons according to another embodiment.

As an example for a plant with a plurality of parallel operated hydrocarbon converters, FIG. 5 shows a further embodiment of plant 30 for generating synthetic functionalised and/or non-functionalised hydrocarbons. FIG. 5 uses the same reference numerals as in earlier embodiments, as far as the same or similar elements are described. In the embodiment shown in FIG. 5, a combination of a high temperature hydrocarbon converter 3a and a low temperature hydrocarbon converter 3b is shown instead of a single hydrocarbon converter 3.

The high temperature hydrocarbon converter 3a comprises a hydrocarbon inlet 4a, a first outlet 5a to discharge carbon and a second outlet 6a to discharge hydrogen. Again, a single outlet 5a may be provided for a mixture (particularly an aerosol) of carbon and hydrogen. The first outlet 5a is connected to the C inlet 11 of the C converter 9 by a connection 8. The optional second outlet 6a of the high temperature hydrocarbon converter 3a is connected to the $H_2$ inlet 33 of the CO converter 31. The high temperature hydrocarbon converter 3a may optionally comprise a further outlet for carbon (not shown in FIG. 5).

The low temperature hydrocarbon converter 3b comprises a process chamber having a hydrocarbon inlet 4b, a first outlet 5b for discharging carbon, a second outlet 6b for discharging hydrogen and an optional third outlet 7b for discharging carbon. Preferably, the low temperature hydrocarbon converter 3b comprises a separation unit for separating hydrogen and carbon after decomposition and for directing the hydrogen and carbon to their respective outlets. The first outlet 5b is optionally connected to the C inlet 11 of the C converter 9 via connection 8, but may also be connected to a carbon collection unit. The second outlet 6b of the low temperature hydrocarbon converter 3b is connected to the $H_2$ inlet 33 of the CO converter 31. The optional third outlet 7b is connected to a carbon collection unit, from which collected carbon may be withdrawn, for instance as carbon black, activated coal or in another form.

As noted above, the $H_2$ inlet 33 of the CO converter 31 and the $H_2$ connections 36a, 36b are optional elements, if the introduction of hydrogen via the $H_2$ connections 36a, 36b is not necessary.

The hydrocarbon introduced into the hydrocarbon inlet 4a and the hydrocarbon introduced into the hydrocarbon inlet 4b may be the same hydrocarbon or may be different hydrocarbons. A hydrocarbon from a first hydrocarbon source may be introduced into the hydrocarbon inlet 4a, for instance natural gas from a natural gas source. However, e.g. synthetically generated functionalised and/or non-functionalised hydrocarbon may be introduced into the hydrocarbon inlet 4b of the low temperature hydrocarbon converter 3b, for instance via the earlier mentioned, optional recycle connection 39. Because of the utilisation of several parallel operated hydrocarbon converters 3, 3a, 3b, the plant 30 may be scaled easier, may be controlled easier and different kinds of carbon may be produced.

Furthermore, the high temperature hydrocarbon converter 3a may for instance be used advantageously to generate "hot" carbon, preferably at a temperature over 1000° C., for the transformation process in the C converter 9. In particular, the high temperature hydrocarbon converter 3a may operate in this case without a separation unit, since the C—$H_2$ mixture, obtained by decomposition, may be introduced directly into the C converter. In this case, the C converter 9 produces a synthesis gas having a C—$H_2$ mixing ratio of e.g. about 1:1 at the outlet.

The low temperature hydrocarbon converter 3b, however, is primarily used in order to provide additional hydrogen for the generation of a synthesis gas or a C—$H_2$ mixture having a C—$H_2$ mixing ratio of greater than 1:3 in the CO converter 31. As no heat transfer from the low temperature hydrocarbon converter 3b to a subsequent process is necessary, the low temperature hydrocarbon converter 3b may advantageously be operated at temperatures below 1000° C. and preferably at the lowest possible temperature.

Thus, a portion of the carbon produced in the hydrocarbon converters 3a, 3b (preferably the portion from the high temperature hydrocarbon converter 3a) may be introduced into the C converter 9 during the operation of plant 30, whereas another portion (preferably the portion from the low temperature hydrocarbon converter 3b) may be diverted from the process as raw material for producing further products. Such products are for instance carbon black or industrial soot, activated coal, special kinds of carbon such as carbon discs and carbon cones etc., which is obtained as black, powdery solid matter. This carbon is an important technical product, which may for instance be used as filler in the rubber industry, as pigment soot for printing colours, inks, paints or as starting material for the production of electrical components, for instance zinc-carbon-batteries, and for the production of cathodes or anodes. Any surplus hydrogen may be diverted for the chemical industry or may be used for generating electricity (by burning or by means of a fuel cell), wherein the low temperature hydrocarbon converter 3b is preferably operated in such a way that it only provides the necessary additional hydrogen.

Figure 6:
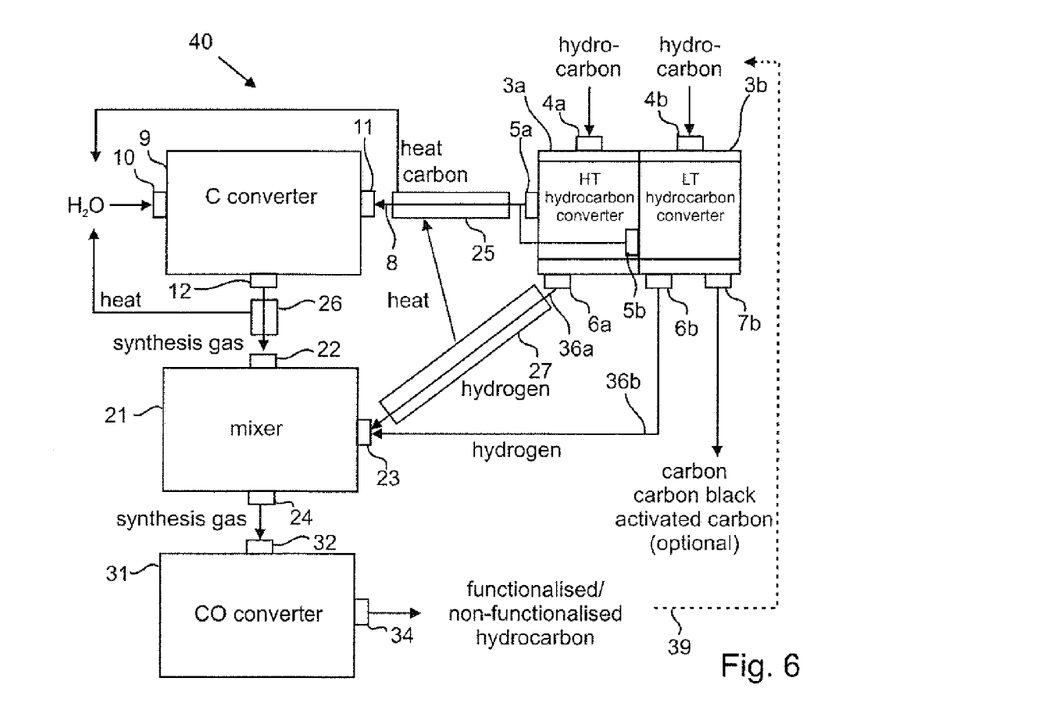
FIG. 6 is a schematic representation of a plant for generating functionalised and/or non-functionalised hydrocarbons according to another embodiment.

FIG. 6 shows an alternative embodiment of the above described plant 40 for generating synthetic functionalised and/or non-functionalised hydrocarbons, for which a plurality of parallel operated high temperature and/or low temperature hydrocarbon converters are provided as well. The plant 40 for generating hydrocarbons shown in FIG. 6 differs from the plant 30 shown in FIG. 5 in such a way that a mixing chamber 21 is located upstream of the CO converter 31. The mixing chamber 21 mixes a synthesis gas specifically adapted to the CO converter 31 and delivers the synthesis gas to the CO converter 31. The elements depicted in FIG. 6 have already been described above and work according to the principles described above. Therefore, no detailed description is given in order to avoid repetitions.

Figure 7:
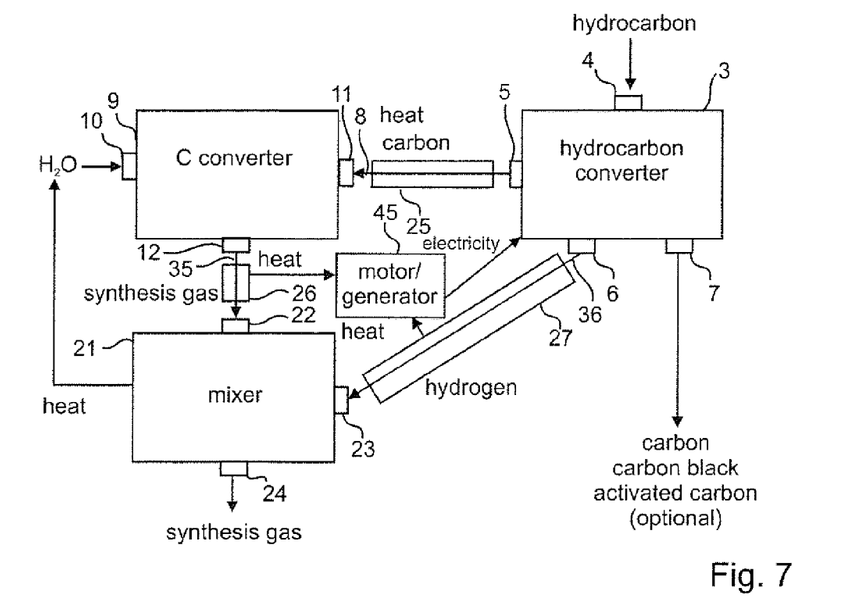
FIG. 7 is a schematic representation of a plant for generating synthetic gas according to another embodiment.
Figure 8:
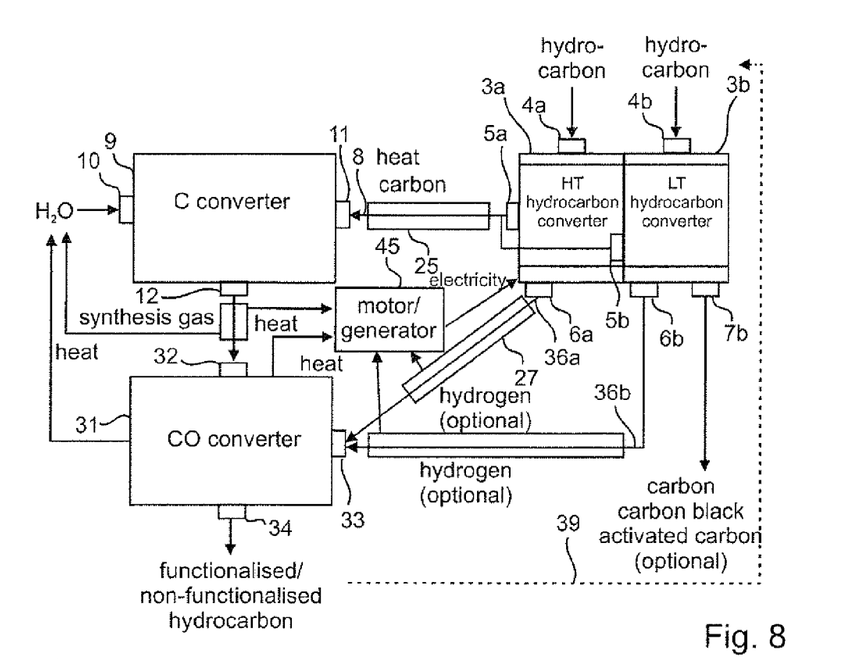
FIG. 8 is a schematic representation of a plant for generating functionalised and/or non-functionalised hydrocarbons according to another embodiment.

FIGS. 7 and 8 show embodiments of the plants 20 and 30 comprising a C heat exchanger unit 25, a synthesis gas heat exchanger unit 26 and a $H_2$ heat exchanger unit 27, wherein each is connected to an engine/generator device 45. The engine/generator device 45 is suitable to at least partially generate electricity from surplus heat from different sections of the plant, wherein said electricity may either be fed into the main grid or that may be used to operate the plant 20, especially the hydrocarbon converter(s). Further, the engine/generator device 45 may be connected to a heat exchanger unit (not shown in FIG. 8), which dissipates the heat generated by the exothermic transformation process taking place inside the CO converter 31. Thus, on the one hand the CO converter may be cooled in a controlled and regulated way, which is advantageous for the operation of the process, and on the other hand electricity may be generated. The engine/generator device 45 may be any device that is suitable to transform heat energy into electricity, for instance a combination of a steam turbine and a generator or a piston engine and a generator.

During operation, the engine/generator device 45 transforms the surplus heat of the plant into electricity, i.e. the heat that is not necessary for carbon-water transformation.

The engine/generator device 45 and the heat exchanger units 25, 26 and 27 are optional elements that can be used at all plants described above. Due to the operation temperature in the respective hydrocarbon converter 3, 3a, 3b, the carbon diverted from the respective second carbon outlets 7, 7a, 7b also contains significant amounts of heat energy. Depending on the desired temperature of the diverted carbon, a large amount of this heat energy may be dissipated by means of heat exchanger units not shown in the figures, and the heat may be reused in the processes described herein and/or may be transformed into electricity using the engine/generator device 45.

In the plants 30 and 40 for generating synthetic functionalised and/or non-functionalised hydrocarbons, cooling of the hydrogen from the hydrocarbon converters 3, 3a, 3b and/or cooling of the synthesis gas from the C converter 9 is performed only as far as the temperature of the hydrocarbons and of the hydrogen does not fall below the operating temperature of the CO converter 31. The operating temperature of the CO converter 31 is usually between 200 and 400° C., depending on the chosen process.

In all plants described above, the hydrocarbon converter 3 may be a high temperature reactor operating at a temperature of more than 1000° C. (e.g. a high temperature Kvaerner reactor) or a low temperature reactor operating at a temperature between 200° C. and 1000° C. (e.g. a low temperature Kvaerner reactor). A presently tested low temperature reactor operates at temperatures between 400 and 900° C. In the case of a low temperature reactor operating at temperatures between 200 and 900° C., it is considered that the introduced carbon is preheated in the connection 8 between the hydrocarbon converter 3 and the C converter 9, as the C converter 9 operates at temperatures between 800 and 1700° C. and preferably 1000 to 1200° C. Further, it becomes clear from FIGS. 7 and 8 that a combination between high temperature and/or low temperature converters may be used in all plants 1, 20, 30 and 40 described above.

In all plants 1, 20, 30 and 40 described above, a portion of the carbon generated in the hydrocarbon converters 3, 3a, 3b may be diverted as carbon black, as activated coal or as another raw material as long as said carbon is not converted in the C converter 9 of plant 1, 20, 30, 40. It shall further be noted that in all of the above described plants, a plurality of C converters may be provided, wherein each of these C converters can transform a portion of the carbon into synthesis gas when water is added. Further, optionally recycling of undesired synthetic functionalised and/or non-functionalised hydrocarbons produced in the CO converter 31 by feeding the undesired hydrocarbons into the hydrocarbon inlets 4, 4a, 4b of the hydrocarbon converter 3 may be carried out in all plants 30 and 40 described above.

In the plants 1, 20, 30, 40 and in the methods for generating synthesis gas and/or synthetic functionalised and/or non-functionalised hydrocarbons, surplus hydrogen may be produced. Surplus hydrogen is left over e.g. with a synthesis gas having low $H_2$ content, and, depending on the synthetic hydrocarbons generated in the CO converter 31, introducing hydrogen into the mixing chamber 21 or the CO converter 31 may be not necessary. In these cases, the surplus or excess hydrogen may be transformed into electricity either directly by means of burning or by means of a fuel cell. Thus, the method may operate substantially without external electricity input. This is particularly advantageous with plants that are operated at remote locations, where a powerful general grid is not available. It should be noted further that a portion of the hydrogen produced in the hydrocarbon converter 3, may be extracted directly from the process and marketed as a commodity.

In all plants, the streams of carbon, synthesis gas and hydrogen and external CO, respectively, between the converters 3, 9, 31 and the mixing chamber 21 may be controlled by means of valves, shutters, sliders etc. Particularly, it is considered that the influx of synthesis gas and hydrogen respectively CO into the CO converter 31 may be controlled by valves. Then, mixing of synthesis gas and hydrogen respectively CO in the desired ratio occurs directly in the CO converter 31.

In all plants described above, the CO converter 31 may consist of a plurality of CO converters (not shown in the figures), wherein the total amounts of the generated and separated hydrogen in the hydrocarbon converters 3, 3a, 3b and the synthesis gas generated in the CO converter 9, may be arbitrarily divided amongst the plurality of CO converters. The individual CO converter have one of the above described designs and mode of operation. The CO converters may have the same design or different designs or modes of operation. In an embodiment having different CO converters, the individual CO converters may each be operated with differently constituted synthesis gas and produce different end products.

To illustrate the methods further, a few examples follow:

Example 1

If 1 part methane is decomposed in the hydrocarbon converter, then one part carbon and two parts hydrogen will be obtained. The carbon reacts with one part water in the C converter and forms one part carbon monoxide and one part hydrogen. After adding 1.1 parts hydrogen, the synthesis gas may be reacted to paraffin in the CO converter. Thereafter, still enough hydrogen is available for cracking the paraffin to Diesel, Otto fuel or kerosine in a further step.

Example 2

If 1 part propane (butane) is decomposed in the hydrocarbon converter, then 3 (4) parts carbon and 4 (5) parts hydrogen will be obtained. The carbon reacts with 3 (4) parts water in the C converter and forms 3 (4) parts carbon monoxide and 3 (4) parts hydrogen. After adding 3.3 (4.4) parts hydrogen, the synthesis gas may be reacted to paraffin in the CO converter. In both cases, the amount of residual hydrogen is just sufficient to crack the paraffin to Diesel, Otto fuel or kerosine in a further step.

Example 3

If 1 part heavy oil (e.g. $C_{20}H_{42}$) is decomposed in the hydrocarbon converter, then 20 parts carbon and 21 parts hydrogen will be obtained. The carbon reacts with 20 parts water in the C converter and forms 20 parts carbon monoxide and 20 parts hydrogen. After adding 21 parts hydrogen, the synthesis gas may be reacted to 20 parts methanol in a different CO converter.

Since, in the here described methods, the hydrogen generated by decomposing hydrocarbons in the hydrocarbon converter 3 is separated from the carbon also formed in the decomposition step, the separated hydrogen may be added in any desired ratio to a synthesis gas having low hydrogen content after forming said synthesis gas having low hydrogen content. Thus, a range of ratios of hydrogen to CO between 1.0 and 3.0 may be achieved. By means of partial oxidation of surplus carbon, a ratio <1.0 may be obtained, and by means of non-utilisation of surplus carbon, a ratio >3.0 may be obtained.

The invention has been explained in some detail with respect to preferred embodiments, wherein the individual features of the described embodiments may be freely combined with each other as far as they are compatible. Also, individual features of the described embodiments may be omitted as far as these features are not absolutely necessary. Many modifications and deviations will be obvious to a person skilled in the art without deviating from the scope of the invention. In a particularly simple embodiment of the plant for generating synthetic functionalised and/or non-functionalised hydrocarbons, the C converter may be designed e.g. as a simple pipe (for instance as an outlet pipe of a high temperature hydrocarbon converter without separation unit), wherein a water inlet leads to said pipe. The water inlet should join said pipe such that the two media streams get well mixed. The pipe should be insulated and could be connected to a heating unit e.g. at an inlet section in order to heat up the pipe, especially at the beginning of the operation to an operating temperature. Further downstream, the pipe could be connected to a heat exchanger adapted to extract surplus heat and to use this heat for heating other sectors of the plant and/or for generating electricity. Additionally, the pipe may comprise an inlet pipe for hydrogen (for instance downstream from the heat exchanger) so that the same pipe not only functions as a C converter, but also functions as a mixing chamber for generating a synthesis gas having a particular mixing ratio. The inlet pipe for hydrogen may originate e.g. from an outlet for hydrogen of a low temperature hydrocarbon converter (having a separation unit). In this case, an output end of the pipe, where a synthesis gas having a predetermined mixing ratio may be discharged, could end in a CO converter.

The invention claimed is:

1. A method for generating synthesis gas comprising the following steps:
    decomposing a hydrocarbon containing fluid into carbon and hydrogen by means of introduction of energy, the energy at least partially being provided by heat, wherein the carbon and the hydrogen have a temperature of at least 200° C. after the decomposing step;
    bringing water into contact with at least a portion of the carbon generated by the decomposing step at a temperature between 800 and 1700° C., wherein upon bringing the carbon into contact with water, the carbon obtained by the decomposing step has cooled down by no more than 50% in ° C. with respect to its temperature after the decomposing step;
    transforming at least a portion of the water and the carbon obtained by the decomposing step into synthesis gas;
    wherein the carbon obtained by the decomposing step and the hydrogen obtained by the decomposing step are jointly brought into contact with the water in form of a carbon hydrogen aerosol and/or;
    wherein the carbon obtained by the decomposing step is separated from the hydrogen obtained by the decomposing step prior to the step of bringing the carbon into contact with the water, and wherein at least a portion of the separated hydrogen is added to the synthesis gas generated by the transformation;
    wherein the carbon obtained by the decomposing step and the hydrogen obtained by the decomposing step are jointly brought into contact with the water in form of an aerosol comprising carbon and hydrogen and/or;
    wherein the carbon obtained by the decomposing step is separated from the hydrogen obtained by the decomposing step prior to the step of bringing the carbon into contact with the water, and wherein at least a portion of the separated hydrogen is added to the synthesis gas generated by the transformation.

2. The method for generating synthesis gas according to claim 1, wherein the decomposing step takes place at a temperature above 1000° C.; and wherein the carbon is brought into contact with the water at a temperature of at least 1000° C., particularly at a temperature between 1000° C. and 1200° C.

3. The method for generating synthesis gas according to claim 1, wherein the heat required to reach the temperature of between 800 and 1700° C. for the transformation originates essentially completely from the heat that is provided for decomposing the hydrocarbon containing fluid.

4. The method for generating synthesis gas according to claim 1, wherein at least a portion of the heat of at least a portion of the carbon obtained by the decomposing step and/or a portion of the hydrogen obtained by the decomposing step is used to heat the water prior to bringing the water in contact with carbon and/or is used to heat the process chamber, in which the water is brought into contact with the carbon.

5. The method for generating synthesis gas according to claim 1, wherein the synthesis gas has a temperature of 800 to 1700° C. after transformation; and wherein at least a portion of its heat is used to preheat the water and/or other media used for the process.

6. The method for generating synthesis gas according to claim 1, wherein at least a portion of the heat of at least a portion of the carbon obtained by the decomposing step and/or a portion of the hydrogen obtained by the decomposing step and/or a portion of the synthesis gas is used for generating electricity, wherein the electricity particularly may be provided as energy carrier for introducing energy for decomposing the hydrocarbon containing fluid.

7. The method for generating synthesis gas according to claim 1, wherein the energy for decomposing the hydrocarbon containing fluid is primarily introduced by means of a plasma.

8. The method for generating synthesis gas according to claim 1, wherein the decomposing step is performed in a Kvaerner reactor.

9. The method for generating synthesis gas according to claim 1, wherein at least a portion of the additional hydrogen is generated by decomposing a hydrocarbon containing fluid at a temperature below 1000° C., particularly below 600° C., by means of a microwave plasma.

10. The method for generating synthesis gas according to claim 1, wherein the ratio of CO to hydrogen of the synthesis gas has a value of 1:1 to 1:3, particularly a value of about 1:2.1.

11. The method for generating synthesis gas according to claim 1 further comprising bringing the synthesis gas into contact with a suitable catalyst in order to cause the transformation of the synthesis gas to synthetic functionalised and/or non-functionalised hydrocarbons, wherein the temperature of the catalyst and/or the synthesis gas is open-loop controlled or close-loop regulated to a predetermined range of temperatures.

12. The method for generating synthesis gas according to claim 11, wherein the transformation of the synthesis gas to synthetic functionalised and/or non-functionalised hydrocarbons is carried out by means of one of the following: a Fischer-Tropsch process, a SMDS process, a Bergius-Pier process, a Pier process, a combination of a Pier process and a MtL process.

13. The method according to claim 1, wherein the hydrocarbon containing fluid to be decomposed is natural gas, methane, wet gases, heavy oil or a mixture thereof.

* * * * *